(12) United States Patent
Kuzma et al.

(10) Patent No.: US 7,050,858 B1
(45) Date of Patent: May 23, 2006

(54) INSERTION TOOL FOR PLACEMENT OF ELECTRODE SYSTEM INSIDE THE COCHLEAR LUMEN

(75) Inventors: Janusz A. Kuzma, Parker, CO (US); Thomas J. Balkany, Coral Gables, FL (US); Chuladatta Thenawara, Castaic, CA (US)

(73) Assignee: Advanced Bionics Corporation, Valencia, CA (US)

( * ) Notice: Subject to any disclaimer, the term of this patent is extended or adjusted under 35 U.S.C. 154(b) by 613 days.

(21) Appl. No.: 10/116,464

(22) Filed: Apr. 3, 2002

Related U.S. Application Data

(60) Provisional application No. 60/281,976, filed on Apr. 6, 2001.

(51) Int. Cl.
*A61N 1/00* (2006.01)

(52) U.S. Cl. ........................... 607/137; 606/129

(58) Field of Classification Search ................ 606/129; 607/116–117, 137; 600/585; 128/898
See application file for complete search history.

(56) References Cited

U.S. PATENT DOCUMENTS

| | | | |
|---|---|---|---|
| 4,010,757 A * | 3/1977 | Jula et al. ................. | 607/119 |
| 4,284,856 A | 8/1981 | Hochmair, et al. | |
| 4,306,560 A * | 12/1981 | Harris ....................... | 606/129 |
| 4,357,497 A | 11/1982 | Hochmair, et al. | |
| 4,898,183 A * | 2/1990 | Kuzma ...................... | 607/137 |
| 5,443,493 A | 8/1995 | Byers, et al. | |
| 6,038,484 A | 3/2000 | Kuzma | |
| 6,078,841 A | 6/2000 | Kuzma | |
| 6,125,302 A | 9/2000 | Kuzma | |
| 6,129,753 A | 10/2000 | Kuzma | |
| 6,149,657 A | 11/2000 | Kuzma | |
| 6,195,586 B1 | 2/2001 | Kuzma | |
| 6,421,569 B1 * | 7/2002 | Treaba et al. ............. | 607/137 |
| 6,544,270 B1 * | 4/2003 | Zhang ....................... | 606/129 |

FOREIGN PATENT DOCUMENTS

WO    WO-02/074211 A1    9/2002

\* cited by examiner

*Primary Examiner*—George Manuel
*Assistant Examiner*—Lenwood Faulcon, Jr.
(74) *Attorney, Agent, or Firm*—Bryant R. Gold; Victoria A. Poissant

(57) ABSTRACT

An insertion tool uses a stylet wire to help guide an electrode system into a cochlea. The insertion tool includes three main elements or parts: a handle, a guide and a slider. The handle is made from light stainless steel tube flattened in front with a machined slot. The guide consists of a plurality of metal tubes, fixed to each other within a holding bracket. In one embodiment, the slider includes a stabilizer wire, a long stylet wire, and a short stylet wire. During the assembly process, the stabilizer and stylet wires are inserted into respective tubes of the guide and the end of the stabilizer wire is bent to form an offset. The electrode system is loaded onto the tool by inserting the short stylet wire into a holder that supports the electrode lead.

33 Claims, 8 Drawing Sheets

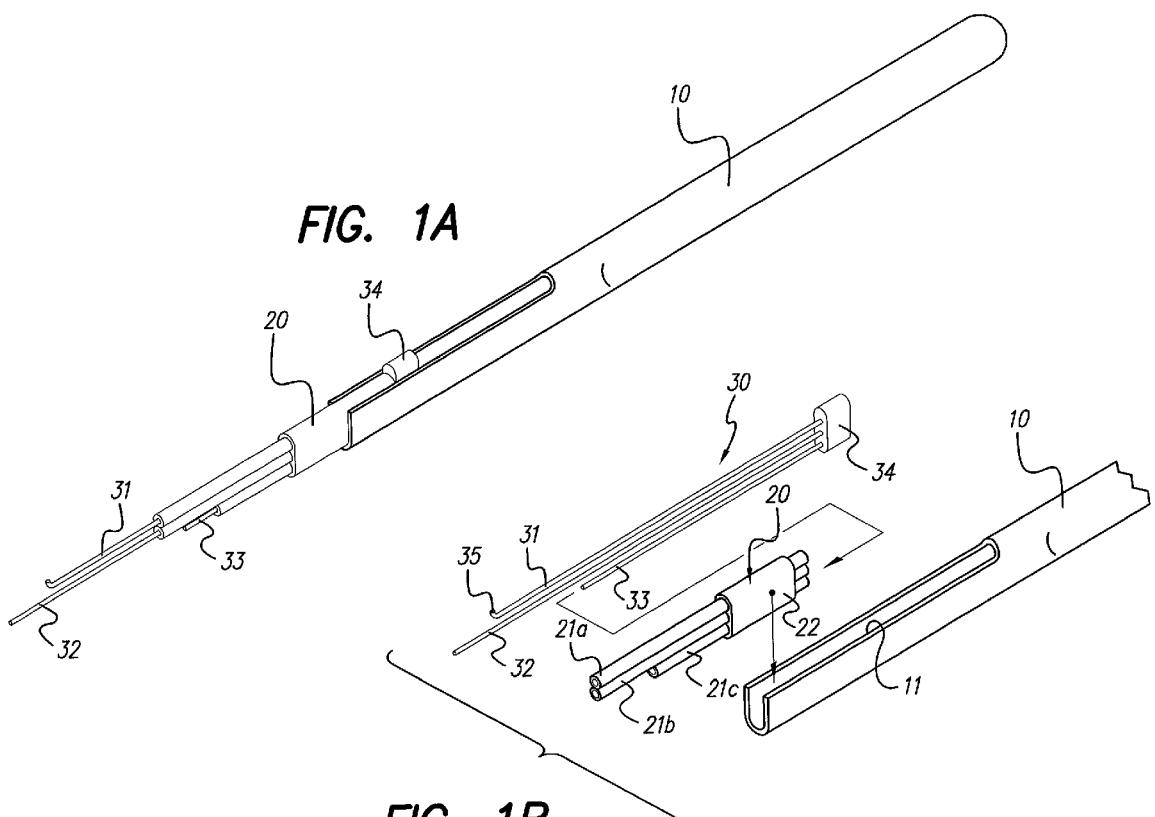

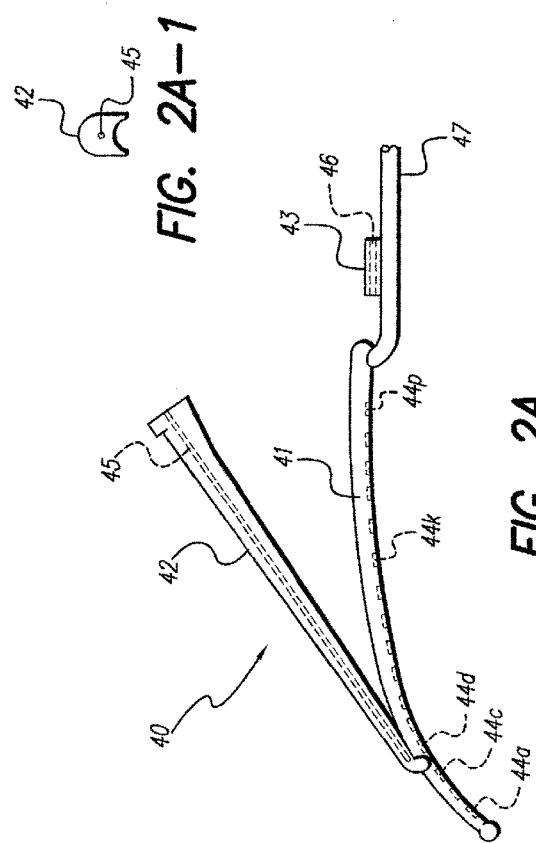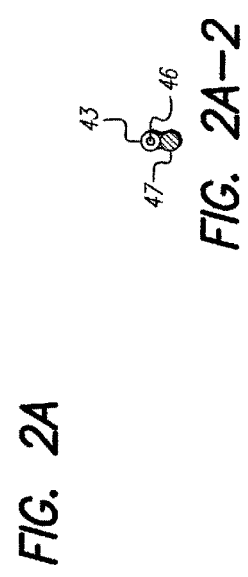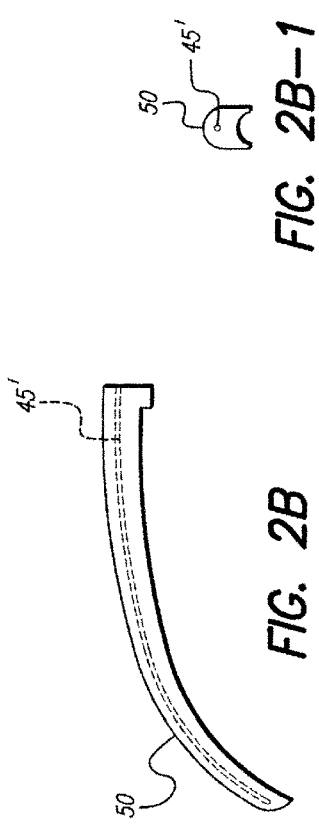

INSERTION TOOL FOR PLACEMENT OF ELECTRODE SYSTEM INSIDE THE COCHLEAR LUMEN

The present application claims the benefit of U.S. Provisional Application Ser. No. 60/281,976, filed Apr. 6, 2001, which application is incorporated herein by reference.

BACKGROUND OF THE INVENTION

The present invention relates to implantable lead systems used with an implantable cochlear stimulator, and more particularly to an insertion tool used to insert an implantable lead system into a human cochlea.

Cochlear electrodes are generally built in the form of elongated, flexible polymer structures with array contacts and connecting wires. It is generally understood that the best performance from a cochlear implant is achieved with the electrode contacts on the cochlear electrode are facing and closely positioned to the modiolar wall of the cochlea.

There are two main types of electrode systems designed to place the electrode contacts in perimodiolar (near or around the modiolus) position. The first is as described in U.S. Pat. No. 6,038,484 or 6,195,586, both of which patents are incorporated herein by reference; and the second is as described in U.S. Pat. No. 6,125,302; also incorporated herein by reference.

To reduce damage to the cochlea structure, electrode carriers are made from very soft, flexible material, and because of this characteristic, they are generally difficult to insert into the cochlea without the use of special supporting tools. An example of such insertion tools is described in U.S. Pat. Nos. 5,443,493 and 6,149,657, both of which patents are also incorporated herein by reference.

The insertion tools described in the referenced patents are designed for use with a particular type of electrode system. Such tools thus do not function adequately with other types of electrode systems. There is thus a need in the art for a more universal insertion tool for use with more than one type of electrode/positioner system.

One type of electrode/positioner system commonly used, referred to herein as the "HiFocus II" electrode, is the type described in U.S. Pat. No. 6,195,586, or electrode/positioner systems similar thereto, wherein a distal tip of the flexible positioner is attached near, but not at, the distal tip of the electrode carrier.

Another type of electrode/positioner system also commonly used, referred to herein as the "HiFocus" electrode, is the type described in U.S. Pat. No. 6,038,484, wherein a flexible positioner and the electrode array, as separate detached elements, are inserted into the cochlea. A preferred electrode array and positioner for use with such a HiFocus electrode are disclosed in U.S. Pat. No. 6,129,753 (electrode array) and U.S. Pat. No. 6,078,841 (positioner), both of which patents are incorporated herein by reference.

Yet another type of electrode system commonly used, referred to herein as the "Highly Pre-curved Electrode", is disclosed in U.S. Pat. No. 6,125,302.

SUMMARY OF THE INVENTION

The present invention addresses the above and other needs by providing an insertion tool wherein a stylet is used to help guide the electrode/positioner system into the cochlea, the stylet being insertable within a lumen of the positioner. Advantageously, in order to minimize damage to the cochlea structure, the stylet is not inserted beyond one half turn of the cochlea. At the one-half turn point, the position of the stylet is stabilized, and the inserted electrode/positioner is pushed off the stylet into the cochlea, followed by the complete withdrawal of the insertion tool.

The insertion tool provided by the present invention includes three main elements or parts: a handle, a guide and a slider. The handle part is preferably made from thin-wall stainless steel tube flattened in front with a machined slot. The guide part consists of three metal tubes, fixed to each other with solder, braze or glue within a holding bracket. The slider part includes a stabilizer made from stainless steel wire, a long stylet wire made from Nitinol wire, and a short stylet wire, also made from Nitinol wire. The stabilizer and stylet wires are fixed together at a proximal end within a knob by brazing, soldering or gluing.

During the assembly process, the stabilizer and stylet wires are inserted into respective tubes of the guide and the end of the stabilizer wire is offset by bending its tip. A sharp edge is made on a forward edge of the bent tip by grinding. The slider assembly and guide assembly are then placed in the front section of the handle and fixed with braze, solder or glue.

The insertion tool provided by the present invention may advantageously be used to insert: (1) the HiFocus electrode/positioner system; (2) the HiFocus II electrode/positioner system; or (3) the Highly Pre-curved Electrode.

BRIEF DESCRIPTION OF THE DRAWINGS

The above and other aspects, features and advantages of the present invention will be more apparent from the following more particular description thereof, presented in conjunction with the following drawings, wherein:

FIGS. 1A and 1B illustrate the construction of the insertion tool;

FIGS. 2A, 2B and 2C depict the types of electrode systems or devices that can be inserted using the insertion tool;

FIGS. 2A-1 and 2A-2 show proximal end views, respectively, of the positioner and electrode of FIG. 2A;

FIGS. 2B-1 similarly shows a proximal end view of the positioner of FIG. 2B;

FIGS. 2C-1 likewise shows a proximal end view of the pre-curved electrode of FIG. 2C;

Corresponding reference characters indicate corresponding components throughout the several views of the drawings.

DETAILED DESCRIPTION OF THE INVENTION

Figure 2C:
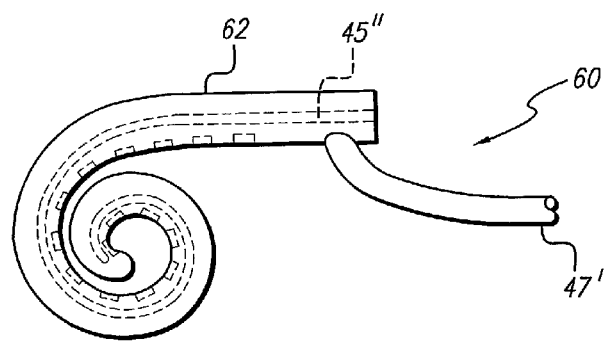

The following description is of the best mode presently contemplated for carrying out the invention. This description is not to be taken in a limiting sense, but is made merely for the purpose of describing the general principles of the invention. The scope of the invention should be determined with reference to the claims.

Clinical experience when using a stylet wire for the insertion of cochlear electrodes has demonstrated that in order to minimize damage to the cochlea structure, it is important not to insert the stylet wire into the cochlea lumen, e.g., the scala tympani, beyond one half turn. At the one half turn point, the position of the stylet wire should be stabilized, and the inserted element, e.g., the positioner or electrode array, should be pushed off the stylet wire into the cochlea, followed by the complete withdrawal of the insertion tool.

The insertion tool provided by the present invention is illustrated in FIGS. 1A and 1B and comprises three main elements or parts: a handle 10, a guide assembly 20 and a slider assembly 30. FIG. 1A shows the handle 10, guide assembly 20 and a knob 34 of the slider assembly 30 all assembled so as to form the insertion tool. FIG. 1B shows an exploded view of the insertion tool, with the handle 10, guide assembly 20 and slider assembly 30 separated from each other.

As seen best in FIG. 1B, the handle 10 is preferably made from a thin-walled metal tube, e.g., a thin-wall stainless steel tube, flattened in front and having a machined slot 11. The slot 11 opens up the tube to form a U-shaped channel in the distal portion of the handle 10, wherein the U-shaped channel has substantially parallel side walls, which parallel side walls represent the flattened portion of the stainless steel tube.

The guide assembly 20 consists, e.g., of three tubes 21a, 21b and 21c, fixed to each other with solder, braze or glue within a holding bracket 22. In one embodiment, the tubes 21a, 21b and 21c are made from metal, e.g., stainless steel. In other embodiments, the tubes 21a, 21b and 21c are made from a suitable biocompatible polymer, such as any of several varieties of biocompatible plastics. In some embodiments, tube 21c may be omitted.

The slider assembly 30 includes a stabilizer rod 31 (referred to hereafter as simply the "stabilizer") made from, e.g., stainless steel wire, a long stylet wire 32 made from Nitinol wire, and a short stylet wire 33, also made from Nitinol wire. The stabilizer 31 and stylet wires 32 and 33 are fixed together at a proximal end within a knob 34 by brazing, soldering or gluing. In some embodiments of the tool, the short stylet wire 33 may be omitted.

During the assembly process, the stabilizer 31 and stylet wires 32 and 33 are inserted into respective tubes 21a, 21b and 21c of the guide assembly 20 and the distal end 35 of the stabilizer wire 31 is bent, forming a bend B. The bend B (shown, e.g., in FIGS. 3 and 4C) provides an offset from the stylet wire 32. A forward edge of the tip 35 of the stabilizer wire 31 is preferably sharpened by grinding or other sharpening action. The slider assembly 30 and guide assembly 20 are then placed in the slot 11 of the front section of the handle 10, and the guide assembly 20 is fixed to the front section of the handle 10 with braze, solder or glue. The slider assembly 30, however, remains free to slide within the slot 11, with the stabilizer 31 and stylet wires 32 and 33 being free to slide within the tubes 21a, 21b and 21c as the knob 34 is slid back and forth within the slot 11.

Next, with respect to FIGS. 2A, 2B and 2C, examples of the different types of cochlear electrode systems that can be inserted using the insertion tool of in FIGS. 1A and 1B are shown.

Figures 1, 2C:
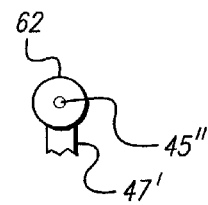

FIG. 2A, for example, shows the HiFocus II Electrode 40 described generally in U.S. Pat. Nos. 6,195,586 and 6,321,125, incorporated herein by reference. The HiFocus II Electrode 40 includes an electrode array 41 having sixteen electrode contacts 44a, 44b, . . . 44p, with the most distal or apical contact being contact 44a, and the most proximal contact being contact 44p. A silicone positioner 42 is connected to the electrode array near its distal end, e.g., with the distal end of the positioner 42 being connected to the electrode array 41 in the vicinity of apical contacts 44c and 44d. The silicon positioner 42 has a lumen 45 passing longitudinally therethrough, with the distal end of the lumen 45 being closed. An end view of the proximal end of the positioner 42 is shown in FIG. 2A-1.

In the example shown in FIG. 2A, an additional silicon tubing section 43 is attached to the lead 47 exiting the electrode array 41, near the proximal end of the array 41. Such attachment of the silicon tubing 43 may be achieved by gluing the tubing section 43 to the front, straight section of the electrode lead 47, as shown in FIG. 2A. The silicon tubing section 43 has a lumen or opening 46 passing therethrough. An end view of the proximal end of the lead 47 is shown in FIG. 2A-2.

The HiFocus II Electrode shown in FIG. 2A is loaded into the insertion tool of FIG. 1A by inserting the long stylet 32 into the lumen 45 within the positioner 42. The short stylet 33 is inserted into the lumen 46 of tubing 43 so as to support the electrode array 41 during the initial stage of insertion.

FIG. 2B shows a separate positioner 50 (not attached to an electrode array), as taught, e.g., in U.S. Pat. No. 6,078,841, used with a HiFocus Electrode of the type taught in U.S. Pat. No. 6,129,753. The positioner 50 has a lumen 45' passing longitudinally therethrough. The lumen 45' is closed at its distal end. An end view of the proximal end of the positioner 50 is shown in FIG. 2B-1.

When the positioner 50 is used with the insertion tool of the present invention, the positioner 50 is inserted into the cochlea using the insertion tool of FIG. 1A by inserting the long stylet 32 into the lumen 45' passing through the body of the positioner 50. The short stylet wire 33 is not used in this instance and may be omitted from the tool.

FIG. 2C shows a Highly Pre-curved Electrode 60 as described in U.S. Pat. No. 6,125,302. The pre-curved electrode 60 includes a pre-curved electrode array 62 at its distal end, which array 62 is attached to a lead 47'. A lumen 45" passes through the pre-curved electrode array 62. An end view of the proximal end of the pre-curved electrode 60 is shown in FIG. 2C-1.

When the pre-curved electrode 60 is inserted into the cochlea using the insertion tool of FIG. 1A, the electrode 60 is preloaded onto the long stylet wire 32 prior to insertion. That is, the long stylet wire 32 is inserted into the lumen 45". When pre-loaded in this manner, the long stylet wire 32 will straighten the pre-curved electrode array, thereby facilitating insertion of the electrode array into the cochlea. As the electrode array is slid off of the long stylet wire within the cochlea, it will resume is pre-curved shape, thereby hugging the modiolus, as desired. The short stylet wire 33 is not used for this operation, and may be omitted.

Figure 3:
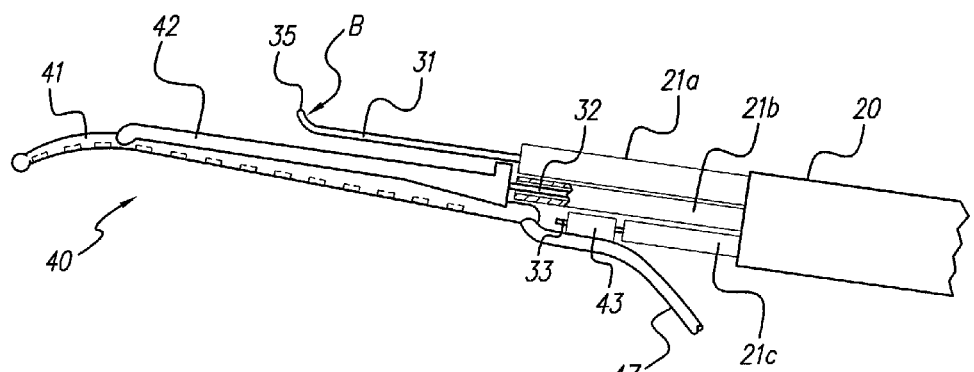
FIG. 3 shows a pre-loaded HiFocus II Electrode in the insertion tool.

Next, with reference to FIG. 3, a HiFocus II Electrode 40 is shown pre-loaded onto the insertion tool of FIG. 1A. The positioner 42 is loaded onto the long stylet wire 32 by moving the knob 34 as far forward as it can go, thereby extending the long stylet wire 32 (as well as the stabilizer 31 and short stylet wire 33) and then threading the long stylet wire 32 into the lumen 45 of the positioner 42. The short stylet wire 33 is similarly threaded through the opening 46 of the tubing section 43 which is attached to the lead 47.

The dynamics of insertion of the HiFocus II Electrode 40 with the insertion tool of the present invention are illustrated schematically in FIGS. 4A, 4B and 4C, explained in more detail below. It is noted that the same dynamics apply when the positioner 50 or the pre-curved electrode 60 are inserted using the insertion tool.

Figure 4A:
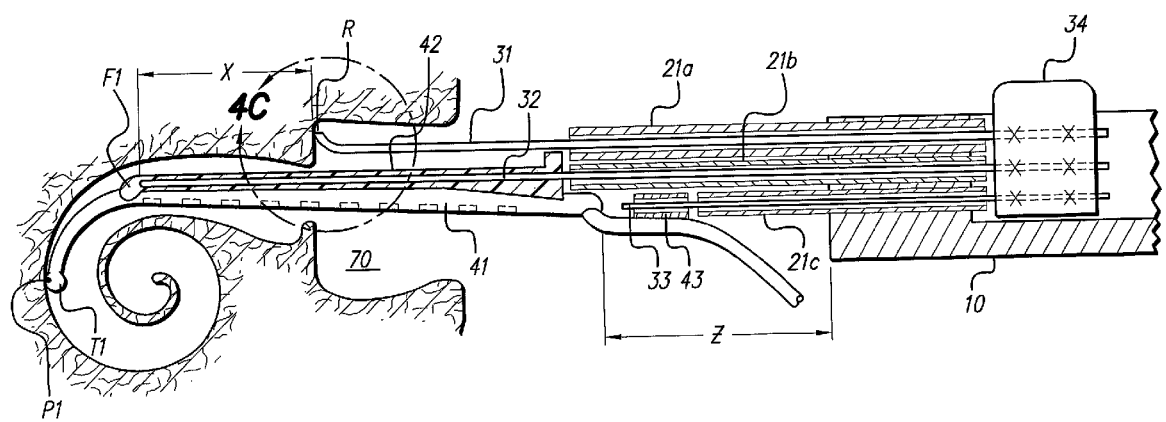
FIGS. 4A and 4B describe the dynamics of insertion for the example of the HiFocus II electrode.
Figure 4B:
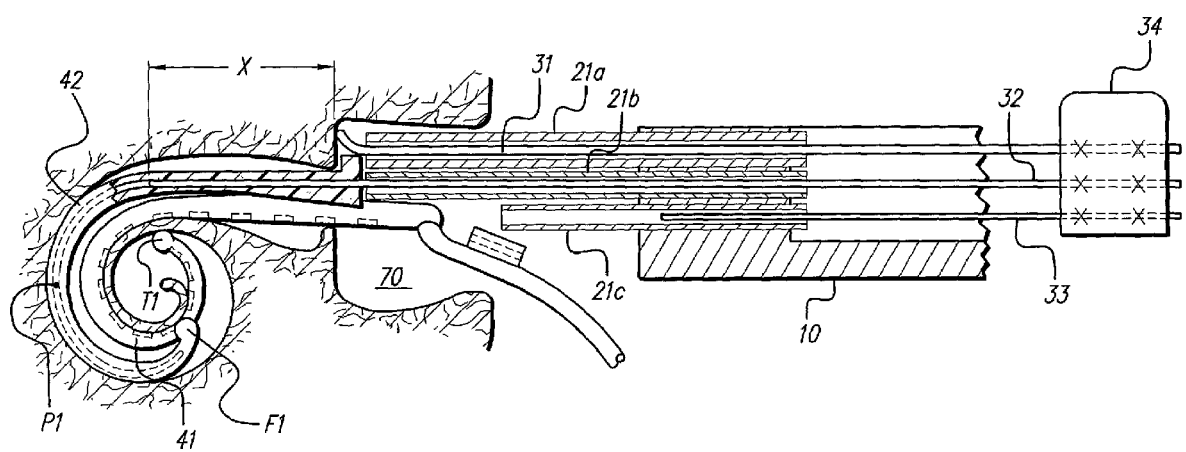
Figure 4C:
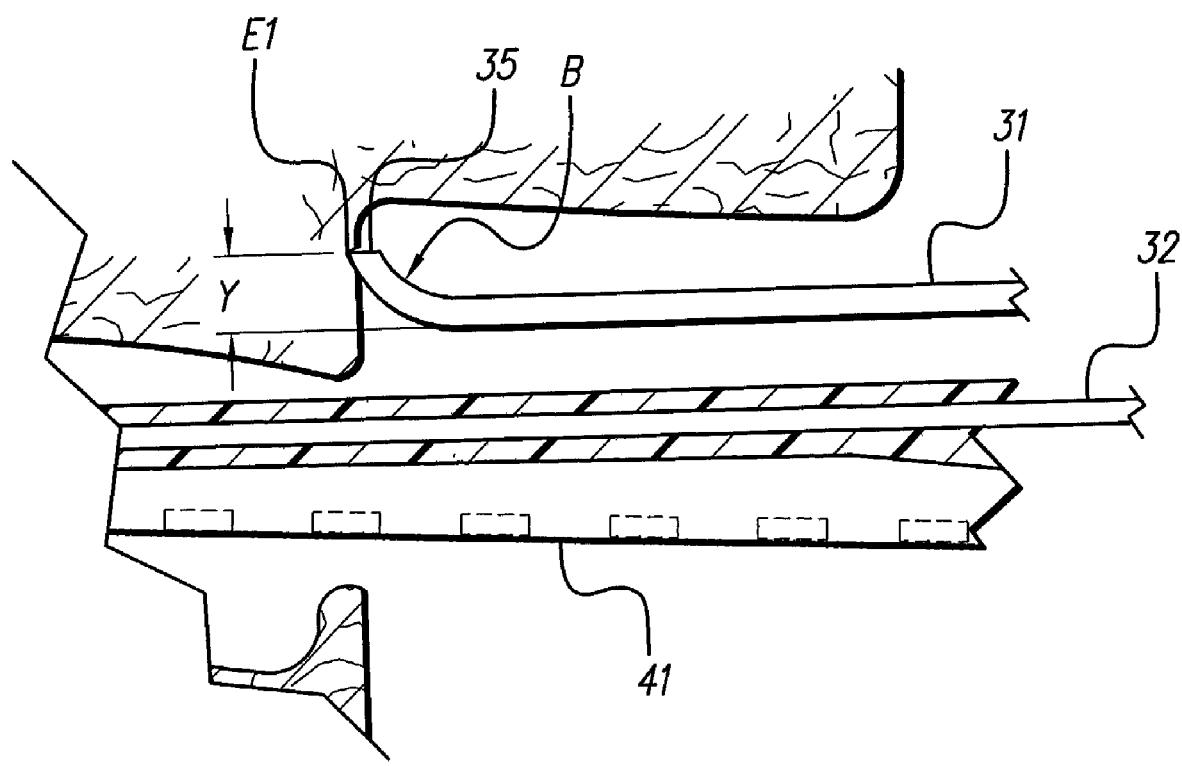
FIG. 4C illustrates an enlarged view of the cochleostomy as the insertion tool is placed thereagainst, and depicts one embodiment of the invention wherein a sharp edge is provided at the end of a stabilizer wire to stabilize the tool in the bone near the cochleostomy in order to maintain the tool's desired position relative to the cochleostomy during the insertion process.

As seen in FIGS. 4A, 4B and 4C, the insertion process is performed in two steps. In the first step, shown in FIG. 4A, the tip of the electrode T1 is inserted into the cochleostomy until the tip of the stabilizer wire 31 rests on the promontory within the facial recess 70 at point R. This resting point R defines and maintains the depth of stylet insertion X into the cochlea.

Moreover, as seen in FIG. 4C, which shows an enlarged view of the cochleostomy within the recess 70, in a preferred embodiment, an edge E1 at the distal end 35 of the stabilizer wire 31 is made to have a sharp point or edge that cuts into the bone and maintains the tool in a stable position during the insertion process. As further seen in FIG. 4C, with the bend B and spacing between the stabilizer wire 31 and the stylet wire 32, there is a distance y that separates the stylet wire 32 from the point where the edge E1 of the distal tip 35 engages the bone in the recess 70. This distance y provides a safe offset from the edge of the cochleostomy to assure that the stabilizer wire 31 does not enter the cochleostomy, and to assure that the stylet wire 32 does enter the cochleostomy.

In the second step, the handle 10 is advanced forward a defined distance Z. During this advancement, the knob 34 moves backward in the slot 11 of the handle 10, although it should be noted that it is not the slider assembly 30 that moves, but rather it is the handle 10 (and guide assembly 20 affixed thereto) that moves. This forward advancement of the handle 10 thus maintains the stabilizer wire 31, long stylet wire 32 and short stylet wire 33 in their fixed positions as the tubes 21a, 21b and 21c of the guide assembly 20 advance forward with the forward advancement of the handle 10 the distance Z. As a result of this movement, the short stylet wire 33 disengages from the tube 43, freeing the electrode lead.

At the same time that the handle 10 is being advanced forward the distance Z, the positioner 42 advances by the same distance into the cochlea. That is, the distal tip of the positioner, located at point F1 shown in FIG. 4A before the handle 10 is advanced forward, moves deeper into the cochlea, as shown in FIG. 4B. As the positioner 42 moves deeper into the cochlea, it pulls the electrode array 41 deeper into the cochlea as well. That is, the distal tip of the electrode array 41, located at point T1 shown in FIG. 4A before the handle 10 is advanced forward, is moved deeper into the cochlea, as shown in FIG. 4B. This action causes the electrode 41 to wrap snugly around the modiolus, which is its preferred position within the cochlea. At that point, i.e., with the positioner 42 and electrode array 41 fully inserted into the cochlea as shown in FIG. 4B, the insertion tool may be withdrawn, leaving the electrode array and positioner in their desired locations fully inserted into the cochlea.

It should also be noted that, in some embodiments, the long stylet wire 32 may be made from a soft or moldable wire, e.g., annealed platinum. In such instance, the softer type of stylet 32 can be extended to about one half turn, corresponding more or less with point P1 of FIGS. 4A and 4B.

Figure 5:
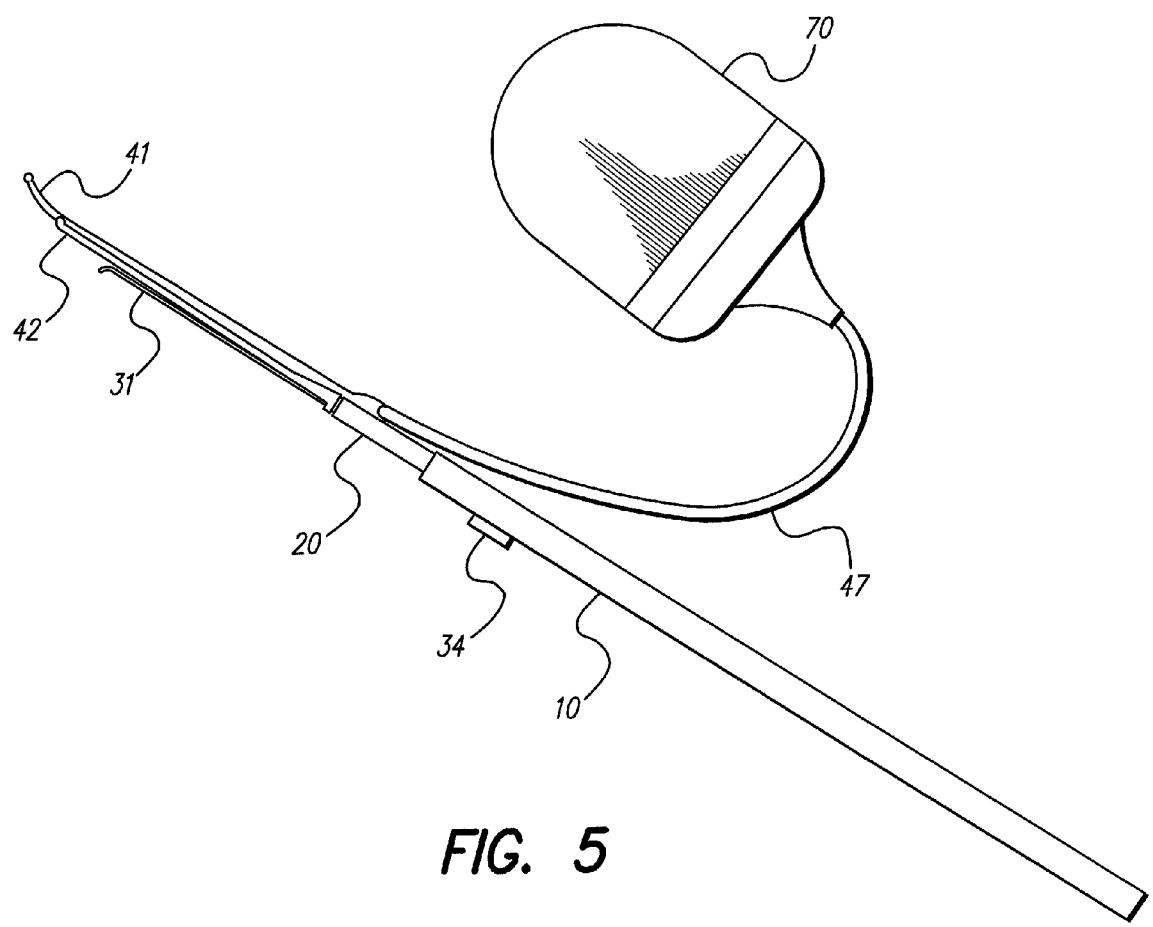
FIG. 5 illustrates a cochlear device, e.g., an implantable cochlear stimulator, wherein the electrode array is pre-loaded into the insertion tool.

FIG. 5 shows a cochlear device, e.g., an implantable cochlear stimulator 70, wherein an electrode array 41 and positioner 42 are pre-loaded onto the insertion tool as shown and described previously in connection with the description of FIGS. 1A, 1B and 3.

Figure 6:
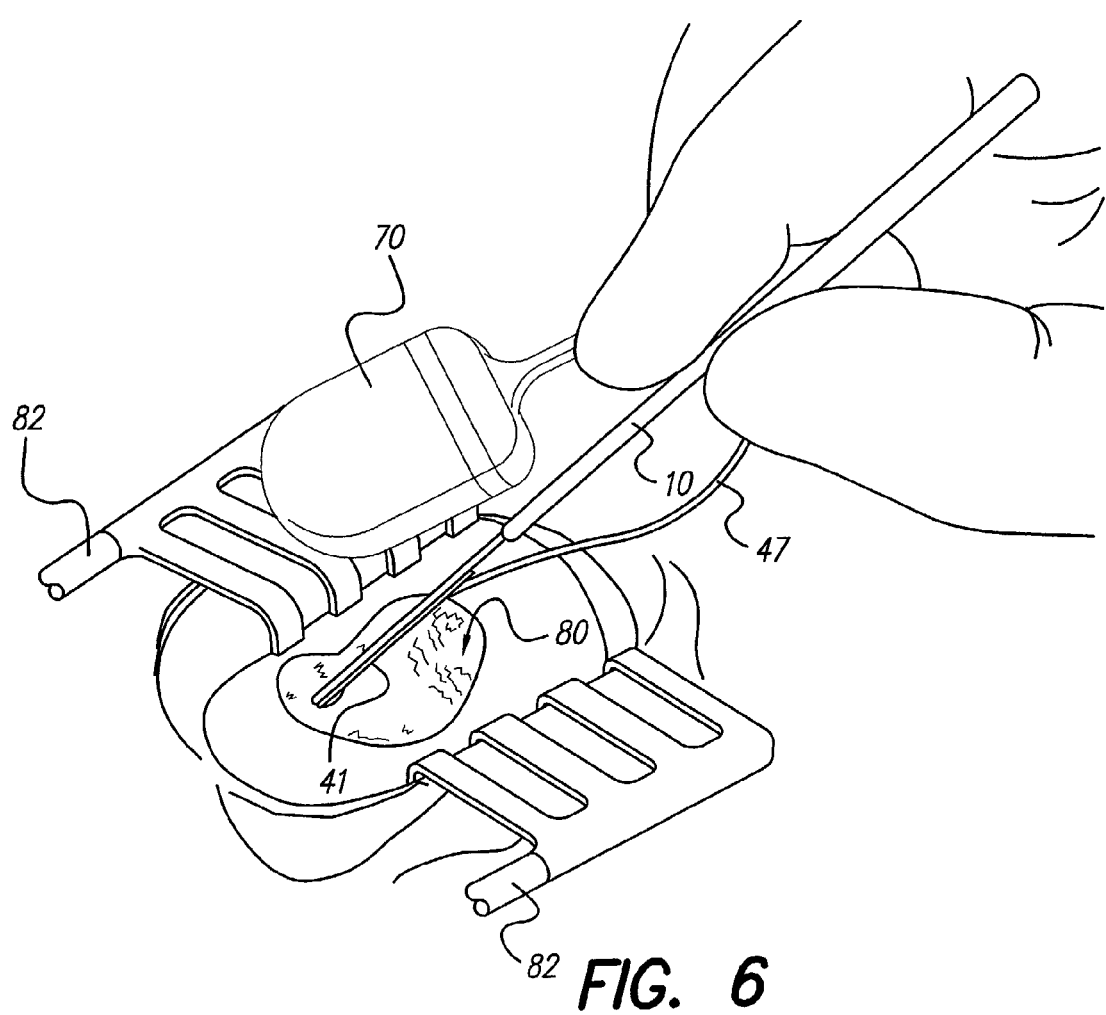
FIG. 6 depicts handling of the insertion tool during the insertion process.

FIG. 6 depicts a preferred manner of handling the insertion tool during the insertion process. As seen in FIG. 6, with the electrode array 41 and positioner 42 (if used) are preloaded onto the insertion tool, the handle 10 is typically held between the thumb and forefinger of the surgeon (or other medical personnel) performing the insertion process. A surgical opening 80 is made in conventional manner, providing access to the point where the cochleostomy is made. Surgical tools 82 hold back the tissue, keeping the opening 80 accessible throughout the surgical procedure. The electrode 41 is carefully inserted into the cochleostomy to the depth set by the stabilizing wire 31 (FIG. 4A). Then, with the stabilizing wire firmly in place, the handle is simply advanced forward as far as it can go (the distance Z in FIG. 4A). At this point the distal end of the tube 21b of the slider assembly 20 has inserted the positioner 42 into the cochlea as far as it can go, thereby preventing further forward advancement, as shown in FIG. 4B. That which is shown in FIG. 4B thus represents the forward-most advancement of the insertion tool, and represents the position where the electrode array and positioner (if used) are fully inserted into the cochlea.

Advantageously, as the positioner 42 is gently pushed or advanced deeper into the cochlea, along an outer (lateral) edge of the cochlea, the electrode array 41 is carried deeper into the cochlea as well. As it is thus carried, the electrode array snugs up against the inner modiolar wall. (Such snugging up against the inner wall may be analogized to a runner running around a track and letting out a rope as he runs. The runner follows the outer track but as he follows the bends of the track the rope will hug the inner track.) That is, although the positioner follows along the lateral wall of the cochlea as it is inserted into the cochlea, the trailing electrode wraps around the inner wall, or modiolus.

Once the fully inserted position illustrated schematically in FIG. 4B has been achieved, the insertion tool is withdrawn, leaving the electrode array and positioner (if used) at their desired locations within the cochlea.

While the invention herein disclosed has been described by means of specific embodiments and applications thereof, numerous modifications and variations could be made thereto by those skilled in the art without departing from the scope of the invention set forth in the claims.

What is claimed is:

1. An insertion tool for inserting an insertable element through a cochleostomy into a cochlea, the insertable element comprising a longitudinal flexible element having a lumen passing longitudinally therethrough into which a stylet wire is insertable, the insertion tool comprising:
   a handle (10);
   a guide assembly (20); and
   a slider assembly (30);
   wherein the guide assembly includes three parallel tubes (21a, 21b, 21c), bonded together within a holding bracket (22); and
   wherein the slider assembly includes a stabilizer wire (31), a long stylet wire (32) and a short stylet wire (33), all connected together at a knob (34) so as to be maintained substantially parallel to each other; and
   wherein the stabilizer wire (31), long stylet wire (32) and short stylet wire (33) are each inserted through respective ones of the three parallel tubes (21*a*, 21*b*, 21*c*), and a distal end of the stabilizer wire includes a bend (B); and wherein the holding bracket (22) of the guide assembly (20) is fixed within a front section of the handle (10); and wherein the slider assembly (30) is slidably engaged with the guide assembly (20); and wherein the long stylet wire (32) is adapted to be inserted into the lumen of the insertable element, and wherein the stabilizer wire (31) has a length adapted to position a distal end of the insertion tool at a desired location relative to the cochleostomy.

2. The insertion tool of claim 1 wherein the distal end of the stabilizer wire (21) includes a sharp edge (E1) adapted to engage with bony tissue adjacent the cochleostomy.

3. The insertion tool of claim 1 wherein the handle (10) is made from a metal tube, and wherein a distal end of the handle has a slot formed therein for receiving the slidable assembly and holding bracket.

4. The insertion tool of claim 3 wherein the distal end of the metal tube whereat the slot is located is flattened to form a U-shaped channel having substantially parallel side walls, and wherein the knob of the slider assembly slidably fits within the U-shaped channel.

5. The insertion tool of claim 4 wherein the metal tube from which the handle is made comprises stainless steel.

6. The insertion tool of claim 1 wherein the three parallel tubes of the guide assembly each comprise a metal tube.

7. The insertion tool of claim 1 wherein the three parallel tubes of the guide assembly each comprise a plastic tube.

8. The insertion tool of claim 1 wherein the stabilizer wire of the slider assembly comprises a stainless steel wire.

9. The insertion tool of claim 8 wherein the long stylet wire and the short stylet wire of the slider assembly each comprise a Nitinol wire.

10. The insertion tool of claim 1 wherein the long stylet wire of the slider assembly comprises a platinum wire, and the short stylet wire of the slider assembly comprises a Nitinol wire.

11. An insertion tool for inserting an insertable element into body tissue, the insertable element comprising a longitudinal flexible element having a lumen passing longitudinally therethrough into which a stylet wire is insertable, the insertion tool comprising:

a handle;

a guide assembly; and a slider assembly, wherein the guide assembly includes a plurality of substantially parallel tubes bonded together within a holding bracket; and wherein the slider assembly includes a plurality of wires, including a stabilizer wire and a stylet wire, all connected together at a knob so as to be maintained substantially parallel to each other; and wherein the stabilizer wire and stylet wire are each inserted through respective ones of the plurality of parallel tubes, and a distal end of the stabilizer wire is bent to form an offset; and wherein the holding bracket of the guide assembly is fixed within a front section of the handle; and wherein the slider assembly is slidably engaged with the guide assembly; and wherein the stylet wire is adapted to be inserted into the lumen of the insertable element, and wherein the stabilizer wire has a length less than the length of the stylet wire, and wherein the stabilizer wire is adapted to position a distal end of the stylet wire at a desired location within the body tissue when a distal end of the stabilizer wire engages the body tissue at a location adjacent the body tissue into which the insertable element is to be inserted.

12. The insertion tool of claim 11 wherein the distal end of the stabilizer wire includes a sharp edge adapted to engage with body tissue as the insertable element is inserted into the body tissue.

13. The insertion tool of claim 11 wherein the handle is made from a metal tube, and wherein a distal end of the handle has a slot formed therein for receiving the slidable assembly and holding bracket.

14. The insertion tool of claim 13 wherein the distal end of the metal tube whereat the slot is located is flattened to form a U-shaped channel having substantially parallel side walls, and wherein the knob of the slider assembly slidably fits within the U-shaped channel.

15. The insertion tool of claim 14 wherein the metal tube from which the handle is made comprises stainless steel.

16. The insertion tool of claim 11 wherein the plurality of parallel tubes of the guide assembly each comprise a metal tube.

17. The insertion tool of claim 11 wherein the stabilizer wire of the slider assembly comprises a stainless steel wire.

18. The insertion tool of claim 1 wherein the stylet wire of the slider assembly comprises a Nitinol wire.

19. The insertion tool of claim 11 wherein the stylet wire of the slider assembly comprises a platinum wire.

20. The insertion tool of claim 11 wherein the body tissue into which the insertable element is adapted to be inserted comprises a cochlea, and wherein the desired location within the cochlea at which a distal end of the stylet wire is to be positioned by the stabilizer wire comprises a location near a first bend of the cochlea, whereby the stylet wire does not have to bend when inserted into the cochlea.

21. A method of inserting an insertable element having a lumen through a cochleostomy into a cochlea using an insertion tool, the insertion tool having a handle, a guide assembly, and a slider assembly; wherein the guide assembly includes a plurality of parallel tubes bonded together within a holding bracket, and wherein the slider assembly is slidably mounted within a front portion of the handle and includes a plurality of wires, including a stabilizer wire and a stylet wire, connected together at a knob; and wherein the stabilizer wire and stylet wire are each inserted through respective ones of the plurality of parallel tubes; and wherein the holding bracket of the guide assembly is fixed within a front portion of the handle; wherein the method comprises:

threading the lumen of the insertable element onto the stylet wire;

inserting a tip of the insertable element and stylet wire into the cochleostomy until the stylet wire has been inserted into the cochlea a prescribed distance X;

moving the handle forward until a distal end of the tube through which the stabilizer wire slides engages the cochleostomy; and pulling the handle of the insertion tool away from the cochleostomy while sliding the insertable element off of the stylet wire, thereby leaving the insertable element inside the cochlea.

22. The method of claim 21 wherein the prescribed distance X comprises less than the one-half turn point of the cochlea, whereby the stylet wire is not required to bend as it is inserted into the cochlea.

23. The method of claim 22 further including setting the prescribed distance X through the use of the stabilizer wire.

24. The method of claim 23 wherein setting the prescribed distance X through the use of the stabilizer wire comprises stopping further insertion of the insertable element and stylet wire into the cochleostomy when a tip of the stabilizer wire engages tissue adjacent the cochleostomy.

25. The method of claim 24 wherein the stylet wire of the insertion tool further includes a sharp edge at its distal tip, and wherein the method further comprises the step of stabilizing the insertion tool at the insertion depth X by sticking the sharp edge of the distal tip of the stabilizer wire into the tissue near the cochleostomy.

26. A method of inserting an elongate, flexible member into a spiraling cochlea channel, wherein a lumen passes longitudinally through at least a portion of the elongate flexible member, the method comprising:
  threading the lumen of the elongate flexible member onto a stylet wire;
  mounting a stabilizer wire so as to be substantially parallel to the stylet wire;
  fixing the length of the stabilizer wire so that a distal tip of the stabilizer engages tissue adjacent an opening of the cochlea channel when the stylet wire has been inserted into the cochlea channel to a desired insertion depth;
  inserting the elongate flexible member and stylet wire into the channel of the cochlea to a depth not beyond a point where the stylet wire has to bend;
  pushing the elongate flexible member off of the stylet wire deeper into the spiraling cochlea channel; and
  stopping further insertion of the elongate flexible member and stylet wire into the cochlea channel when the tip of the stabilizer wire engages the tissue adjacent the opening of the cochlea channel.

27. The method of claim 26 further including forming a bend in the stabilizer wire near its distal tip.

28. An insertion tool for inserting an elongate, flexible member into a spiraling cochlear channel, wherein a lumen passes longitudinally through at least a portion of the elongate flexible member, the insertion tool comprising:
  a stylet wire;
  a stabilizer wire held substantially parallel to the stylet wire, wherein the stabilizer wire has a length less than the stylet wire by a distance X;
  a distal tip of the stabilizer wire;
  means for engaging the distal tip of the stabilizer wire to body tissue near an opening of the cochlea;
  means for threading the lumen of the elongate flexible member onto the stylet wire;
  means for inserting the stylet wire, with the elongate flexible member threaded thereon, into the spiraling cochlear channel to a prescribed depth;
  means for pushing the elongate flexible member off of the stylet wire into the spiraling cochlea channel; and
  means for determining the difference in length X between the stylet wire and stabilizer wire to a prescribed depth in which the stylet wire is inserted into the channel of the cochlea.

29. The insertion tool of claim 28 wherein the distance X is adapted to position a tip fo the stylet wire at a location not beyond a first half turn of the spiraling cochlear channel.

30. The insertion tool of claim 28 wherein the stylet wire is made from a soft bendable substance, and wherein the distance X is adapted to position a tip of the stylet wire at a location beyond the first half turn of the spiraling cochlear channel.

31. An insertion tool adapted for inserting an elongate electrode array having a lumen through a cochleostomy into a cochlea comprising:
  a handle;
  a slider assembly supported by the handle; and
  a stabilizer wire protruding from the slider assembly;
  wherein the slider assembly is mounted for slidable movement relative to the handle, and includes a protruding stylet wire wherein the stylet wire may be extended or retracted relative to the handle through movement of the slider assembly relative to the handle;
  wherein when the stylet wire is extended and the lumen of the elongate electrode array is threaded onto the extended stylet wire, the stylet wire may be withdrawn from the lumen through movement of the slider assembly relative to the handle at the same time that the electrode array is slid off of the stylet wire; and
  wherein the stabilizer wire providing a means for stabilizing the insertion tool against the cochleostomy during use of the insertion tool.

32. The insertion tool of claim 31 further including a guide assembly affixed to a proximal end of the handle, wherein the guide assembly includes a tube structure, and wherein the stylet wire passes through the tube.

33. The insertion tool of claim 32 wherein a distal end of the tube structure of the guide assembly pushes the elongate electrode array off of the stylet wire when the slider assembly is moved proximally relative to the handle.

* * * * *